United States Patent [19]
Brazdil, Jr. et al.

[11] Patent Number: 6,087,524
[45] Date of Patent: Jul. 11, 2000

[54] PREPARATION OF VANADIUM ANTIMONATE BASED CATALYSTS USING $SNO_2 \cdot XH_2O$

[75] Inventors: James Frank Brazdil, Jr.; Joseph Peter Bartek, both of Highland Heights, Ohio

[73] Assignee: The Standard Oil Company, Chicago, Ill.

[21] Appl. No.: 09/293,452

[22] Filed: Apr. 16, 1999

Related U.S. Application Data

[62] Division of application No. 09/151,463, Nov. 9, 1998, Pat. No. 5,972,833, which is a continuation of application No. 08/785,543, Jan. 17, 1997, Pat. No. 5,854,172.

[51] Int. Cl.[7] .................................................. C07C 253/00
[52] U.S. Cl. ........................ 558/320; 558/321; 558/322; 558/323; 558/324; 558/325
[58] Field of Search ..................... 558/320–325

[56] References Cited

U.S. PATENT DOCUMENTS

| | | | |
|---|---|---|---|
| 3,681,421 | 8/1972 | Barclay et al. | 558/325 |
| 3,879,435 | 4/1975 | Gasson et al. | 558/325 |
| 3,914,278 | 10/1975 | Gasson et al. | 558/322 |
| 4,139,552 | 2/1979 | Grasselli et al. | 260/465.3 |
| 4,767,739 | 8/1988 | Glaeser et al. | 502/209 |
| 4,877,764 | 10/1989 | Glaeser et al. | 502/209 |
| 5,079,207 | 1/1992 | Brazdil et al. | 502/206 |
| 5,214,016 | 5/1993 | Brazdil et al. | 502/202 |
| 5,258,543 | 11/1993 | Suresh et al. | 558/325 |
| 5,576,469 | 11/1996 | Brazdil, Jr. et al. | 558/319 |
| 5,866,502 | 2/1999 | Cirjak et al. | 502/353 |

Primary Examiner—Mark L. Bell
Assistant Examiner—Patricia L. Hailey
Attorney, Agent, or Firm—David P. Yusko

[57] ABSTRACT

A method of preparing a catalyst having the elements and the proportions indicated by the following empirical formula:

$$VSb_m A_a D_d O_x$$

where
  A is one or more Ti, Sn, where Sn is always present
  D is one or more Li, Mg, Ca, Sr, Ba, Co, Fe, Cr, Ga, Ni, Zn, Ge, Nb, Zr, Mo, W, Cu, Te, Ta, Se, Bi, Ce, In, As, B, Al and Mn wherein
  m is 0.5 to 10
  a is greater than zero to 10
  d is zero to 10
  x is determined by the oxidation state of the cations present, comprising making an aqueous slurry of a mixture of source batch materials comprising compounds of said elements to be included in the final catalyst, followed by drying and heat calcining the mixture to an active catalyst, wherein the source batch material for the tin is a solution which comprises $SnO_2 \cdot xH_2O$ wherein $x \geq 0$ dispersed in tetraalkyl ammonium hydroxide wherein the tetraalkyl ammonium hydroxide is defined by the following formula:

$$C_n H_{2n+1} NOH$$

wherein $5 \geq n \geq 1$,
drying said slurry and calcining the mixture to an upper calcination temperature of at least 500° C.

3 Claims, No Drawings

PREPARATION OF VANADIUM ANTIMONATE BASED CATALYSTS USING $SnO_2 \cdot XH_2O$

This is a division of application Ser. No. 09/151,463, filed on Nov. 9, 1998, now U.S. Pat. No. 5,972,833 which in turn is a continuation of Ser. No. 08/785,543, filed Jan. 17, 1997, now U.S. Pat. No. 5,854,172.

BACKGROUND OF THE INVENTION

Field of the Invention

This invention relates to a method for the preparation of tin-containing vanadium-antimony oxide catalysts useful for the catalytic ammoxidation of $C_3$ to $C_5$ paraffins or olefins, more specifically for the preparation of catalysts for the ammoxidation of propane or isobutane or propylene or isobutylene to its corresponding $\alpha,\beta$-unsaturated mononitrile, acrylonitrile or methacrylonitrile. In addition, the catalyst may be used in the ammoxidation of methylpyridine, m-xylene or the oxidation of o-xylene to cyanopyridine, isophthalonitrile or phthalic anhydride, respectively.

More specifically, the invention relates to the use of a $SnO_2 \cdot xH_2O$ wherein $x \geq 0$ dispersed in a solution of a tetraalkyl ammonium hydroxide as the reagent for tin in the preparation of catalysts containing vanadium and antimony and tin in oxide form. These types of catalysts are disclosed for instance in U.S. Pat. Nos. 3,681,421, 4,788,317, 5,008,427 and in British specifications 1,336,135 and 1,336,136, published in November 1973.

Not all sources of tin are equally effective as promoters in vanadium-antimony oxide catalysts for the oxidation and ammoxidation of saturated $C_3$ and $C_4$ alkanes, particularly ammoxidation. In fact, U.S. Pat. No. 5,214,016 and EPO 691306-A1 teach that the source of tin promoter is critical to the performance characteristics of the finished catalyst. It is believed that the tin should be present in very finely divided form in the precursors of such catalysts in order for the tin to be fully reactive when the solid state reaction takes place upon calcination of the catalyst precursor mixture. Tin oxide sol is a suitable source in making catalysts of the present invention; see U.S. Pat. No. 5,008,427. However, ground tin oxide or tin oxide made by reacting tin metal with nitric acid are decidedly less effective sources in catalyst preparation. While current commercially available tin oxide sol is effective, it has a serious disadvantage because it is a very expensive source.

SUMMARY OF THE PRESENT INVENTION

It is an object of the present invention to provide a method of making a superior oxidation (particularly ammoxidation) catalyst while avoiding the use of current commercially available tin oxide sols.

It is another object of the invention to make such a catalyst at a fraction of the expense with respect to the tin component as compared to using current commercially available tin oxide sol as the source of tin in the catalyst precursor.

Other objects, as well as aspects, features and advantages, of the invention will become apparent from a study of the specification including the specific examples.

The foregoing and other objects are accomplished by the present invention according to which there is provided a method of making a catalyst containing vanadium, antimony and tin in the oxide state which comprises making an aqueous slurry of a mixture of source batch materials comprising compounds of the elements to be included in the final catalyst, followed by drying and calcining the mixture to form an active catalyst, wherein the source batch material for the tin is a solution which comprises $SnO_2 \cdot xH_2O$ wherein $x \geq 0$ dispersed in tetraalkyl ammonium hydroxide wherein the tetraalkyl ammonium hydroxide is defined by the following formula:

$$(C_nH_{2n+1})_4NOH$$

wherein $5 \geq n \geq 1$.

Preferably, tetramethyl ammonium hydroxide is utilized in the practice of the invention.

The catalyst can be made from any suitable organic or inorganic precursor compounds of V and Sb, and compounds used to introduce other optional elements into the final catalyst after calcination, as is well known in the art, such as the salts, oxides, hydroxides or metallo-organic compounds of such elements, with the tin being introduced to the batch of raw materials for preparing such catalysts in the form of a solution of $SnO_2 \cdot xH_2O$ dispersed in tetraalkyl ammonium hydroxide as previously disclosed herein. The batch mixture of precursor materials is heated and calcined in a known manner until the final catalyst results. Examples of such raw source batch materials are of course shown in the specific working examples herein.

Particularly effective procedures for the manufacture of the catalyst are set forth in U.S. Pat. Nos. 4,784,979, 4,879,264, 3,860,534 and 5,094,989, herein incorporated by reference. In addition, the catalyst may optionally be treated by one or more of the methods disclosed in U.S. Pat. Nos. 5,432,141 and 5,498,588, also herein incorporated by reference.

In making the catalysts of the present invention, the upper calcining temperature is usually at least 500° C., but for ammoxidation of paraffins this temperature is preferably over 750° C., most often at least 780° C.

The catalyst may be unsupported or supported on a suitable carrier. Preferably the catalyst is supported on a carrier such as silica, alumina, silica alumina, zirconia or mixtures thereof.

A preferred method of the invention is to make catalysts having the elements and the proportions indicated by the empirical formula:

$$VSb_mA_aD_dO_x$$

where
A is one or more Ti, Sn, where Sn is always present
is one or more Li, Mg, Ca, Sr, Ba, Co, Fe, Cr, Ga, Ni, Zn, Ge, Nb, Zr, Mo, W, Cu, Te, Ta, Se, Bi, Ce, In, As, B, Al and Mn wherein
m is 0.5 to 10
a is greater than zero to 10
d is zero to 10
x is determined by the oxidation state of the cations present, which comprises making an aqueous slurry of a mixture of source batch materials comprising compounds of said elements to be included in the final catalyst, followed by drying and heat calcining the mixture to an active catalyst, wherein the source batch material for the tin is a solution which comprises $SnO_2 \cdot xH_2O$ wherein $x \geq 0$ dispersed in tetraalkyl ammonium hydroxide wherein the tetraalkyl ammonium hydroxide is defined by the following formula:

$(C_nH_{2n+1})_4NOH$ wherein $5 \geq n \geq 1$,
drying said slurry and calcining the mixture to an upper calcination temperature of at least 780° C. The upper calcination temperature can be up to 1200° C., but is most often not over 1050° C.

In another aspect of the present invention, there is provided a process for making an α,β-unsaturated mononitrile selected from acrylonitrile and methacrylonitrile, by the catalytic reaction in the vapor phase of a paraffin selected from propane and isobutane with molecular oxygen and ammonia and optionally a gaseous diluent, by catalytic contact of the foregoing reactants in a reaction zone with a catalyst, the feed to said reaction zone containing a mole ratio of said paraffin to $NH_3$ in the range from 2.5 to 16 (preferably 4 to 12; especially preferred being 5 to 11) and a mole ratio of said paraffin to $O_2$ in the range from 1 to 10 (preferably 2 to 9, especially preferred being 3 to 9), said catalyst having the empirical composition recited in the last previous paragraph, said catalyst having been made by the method of the last previous paragraph.

The catalyst may also be used in the ammoxidation of methylpyridine and m-xylene to cyanopyridine and isophthalonitrile or the oxidation of o-xylene to phthalic anhydride. The mole ratios of $NH_3$ to methylpyridine and $O_2$ to methylpyridine are 1 to 5 and 1 to 10, respectively. The mole ratios of $NH_3$ to m-xylene and $O_2$ to m-xylene are 1 to 5 and 1 to 10, respectively. In the phthalic anhydride reaction, the ratio of $O_2$ to o-xylene may range from 1 to 10.

The catalyst prepared by the process of the present invention may also be utilized in the ammoxidation of propylene or isobutene with ammonia and oxygen to produce acrylonitrile or methacrylonitrile. The mole ratio of $NH_3$ to olefin may range from about 1 to 5 and the mole ratio of $O_2$ to olefin may range from 1 to 10 in this reaction under conventional temperatures and conditions well known in the art.

DETAILED DESCRIPTION OF THE INVENTION

The following examples of making the catalysts and the ammoxidation reactions using the catalysts so made are exemplary only and should not be understood to be in any way limiting.

EXAMPLE 1

A catalyst having the composition $VSb_{1.4}Sn_{0.2}Ti_{0.1}O_x$ (Catalyst No. 17388-79) was prepared by mixing 27.30 g of $V_2O_5$ powder with a solution consisting of 100 ml of 30% $H_2O_2$ in 900 ml of water in a two liter beaker. After reaction of the $V_2O_5$ powder was complete, 61.25 g of $Sb_2O_3$ was added followed by 2.40 g of $TiO_2$ powder (Degussa P-25). The beaker was covered with a watch glass and the mixture was stirred and heated for about 3 hours. In a separate beaker, 10.13 g of $SnO_2 \cdot xH_2O$ ("acid tin oxide" Magnesium Elektron Inc., received Jun. 7, 1991) were added to 100 ml of water and 8 ml of 25 wt % solution of tetramethyl ammonium hydroxide. The mixture was heated on a hot plate with constant stirring until a translucent mixture formed. This tin-containing dispersion was then added to the foregoing vanadium, antimony, titanium dispersion. The mixture was stirred in an uncovered beaker with heating in order to reduce the volume by evaporation of water. When the mixture could no longer be stirred, it was dried in an oven at 120° C. Thereafter, it was calcined for 1 hour at 325° C. then for 8 hours at 650° C., then cooled and crushed and sieved and the 20–35 mesh particles collected. A portion of this was calcined for 3 hours at 820° C. then at 650° C. for an additional 3 hours.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This washing was done a total of three times. After the last of the isobutanol was passed through the funnel, the catalyst was heated in an oven at 120° C. to remove the residual isobutanol on the catalyst.

The catalyst was evaluated for ammoxidation of propane using a ¼" titanium U-tube fixed bed reactor. The gaseous feed to the reactor had a molar ratio of 3 propane/1 ammonia/2 oxygen/5 nitrogen at 15 psig pressure. At a reactor temperature of 490° C. and a contact time of 1.4 seconds, selectivity to acrylonitrile was 61.2% at a propane conversion of 19.2%. At a reactor temperature of 495° C. and a contact time of 1.4 seconds, selectivity to acrylonitrile was 58.6% at a propane conversion of 21.2%.

EXAMPLE 2

A catalyst having the composition $VSb_{1.4}Sn_{0.2}Ti_{0.1}O_x$ was prepared by mixing 27.30 g of $V_2O_5$ powder with a solution consisting of 100 ml of 30% $H_2O_2$ in 900 ml of water in a two liter beaker. After reaction of the $V_2O_5$ powder was complete, 61.25 g of $Sb_2O_3$ was added followed by 2.40 g of $TiO_2$ powder (Degussa P-25). The beaker was covered with a watch glass and the mixture was stirred and heated for about 3 hours. In a separate beaker, 10.13 g of $SnO_2 \cdot xH_2O$ ("acid tin oxide" Magnesium Elektron Inc., received Jun. 7, 1991) were added to 100 ml of water and 30 ml of 25 wt % solution of tetramethyl ammonium hydroxide. The mixture was heated on a hot plate with constant stirring until a translucent mixture formed. This tin-containing dispersion was then added to the foregoing vanadium, antimony, titanium dispersion. The mixture was stirred in an uncovered beaker with heating in order to reduce the volume by evaporation of water. When the mixture could no longer be stirred, it was dried in an oven at 120° C. Thereafter it was calcined for 1 hour at 325° C., then for 8 hours at 650° C., then cooled and crushed and sieved and the 20–35 mesh particles collected. A portion of this was calcined for 3 hours at 820° C. then at 650° C. for an additional 3 hours.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This washing was done a total of three times. After the last of the isobutanol was passed through the funnel, the catalyst was heated in an oven at 120° to remove the residual isobutanol on the catalyst.

The catalyst was evaluated for ammoxidation of propane using a ¼" titanium U-tube fixed bed reactor. The gaseous feed to the reactor had a molar ratio of 3 propane/1 ammonia/2 oxygen/5 nitrogen at 15 psig pressure. At a reactor temperature of 495° C. and a contact time of 2.4 seconds, selectivity to acrylonitrile was 55.6% at a propane conversion of 13.1%.

What is claimed is:

1. A process for making an α,β-unsaturated mononitrile selected from acrylonitrile and methacrylonitrile, by reacting in the vapor phase a paraffin selected from propane and isobutane with molecular oxygen and ammonia, in a reaction zone, in contact with a catalyst having the following formula $$VSb_mA_aD_dO_x$$

where
A is one or more Ti, Sn, where Sn is always present
D is one or more Li, Mg, Ca, Sr, Ba, Co, Fe, Cr, Ga, Ni, Zn, Ge, Nb, Zr, Mo, W, Cu, Te, Ta, Se, Bi, Ce, In, As, B, Al and Mn wherein
m is 0.5 to 10
a is greater than zero to 10
d is zero to 10
x is determined by the oxidation state of the cations present, the feed to said reaction zone containing a mole ratio of said paraffin to $NH_3$ in the range from 2.5 to 16 and a mole ratio of said paraffin to $O_2$ in the range from 1 to 10, wherein the catalyst has been prepared by making an aqueous slurry of a mixture of source batch materials comprising compounds of the elements to be included in the final catalyst, drying the mixture, and calcining the mixture to form an active catalyst, wherein the source batch material for the tin is a solution which comprises $SnO_2 \cdot xH_2O$ wherein $x \geq 0$ dispersed in tetraalkyl ammonium hydroxide wherein the tetraalkyl ammonium hydroxide is defined by the following formula:

$$(C_nH_{2n+1})_4NOH$$

wherein $5 \geq n \geq 1$.

2. A process for making an α,β-unsaturated mononitrile selected from acrylonitrile and methacrylonitrile, by the catalytic reaction in the vapor phase of a paraffin selected from propane and isobutane with molecular oxygen and ammonia by catalytic contact of the foregoing reactants in a reaction zone with a catalyst having the following formula:

$$VSb_mA_aD_dO_x$$

where
A is one or more Ti, Sn, where Sn is always present
D is one or more Li, Mg, Ca, Sr, Ba, Co, Fe, Cr, Ga, Ni, Zn, Ge, Nb, Zr, Mo, W, Cu, Te, Ta, Se, Bi, Ce, In, As, B, Al and Mn wherein
m is 0.5 to 10
a is greater than zero to 10
d is zero to 10
x is determined by the oxidation state of the cations present, the feed to said reaction zone containing a mole ratio of said paraffin to $NH_3$ in the range from 2.5 to 16 and a mole ratio of said paraffin to $O_2$ in the range from 1 to 10, wherein the catalyst has been prepared by making an aqueous slurry of a mixture of source batch materials comprising compounds of the elements to be included in the final catalyst, drying the mixture, and calcining the mixture to form an active catalyst, wherein the source batch material for the tin is a solution which comprises $SnO_2 \cdot xH_2O$ wherein $x \geq 0$ dispersed in tetraalkyl ammonium hydroxide wherein the tetraalkyl ammonium hydroxide is defined by the following formula:

$$(C_nH_{2n+1})_4NOH$$

wherein $5 \geq n \geq 1$.

3. A process for making an α,β-unsaturated mononitrile selected from acrylonitrile and methacrylonitrile by the catalytic reaction in the vapor phase of an olefin selected from propylene and isobutene with ammonia, and an oxygen containing gas by catalytic contact of the foregoing reactants in a reaction zone with a catalyst having the following formula:

$$VSb_mA_aD_dO_x$$

where
A is one or more Ti, Sn, where Sn is always present
D is one or more Li, Mg, Ca, Sr, Ba, Co, Fe, Cr, Ga, Ni, Zn, Ge, Nb, Zr, Mo, W, Cu, Te, Ta, Se, Bi, Ce, In, As, B, Al and Mn wherein
m is 0.5 to 10
a is greater than zero to 10
d is zero to 10
x is determined by the oxidation state of the cations present, the feed to said reaction zone containing a mole ratio of ammonia to said olefin in the range from 1 to 5, and a mole ratio of oxygen to said olefin in the range form 1 to 10 wherein the catalyst has been prepared by making an aqueous slurry of a mixture of source batch materials comprising compounds of the elements to be included in the final catalyst, drying the mixture, and calcining the mixture to form an active catalyst, wherein the source batch material for the tin is a solution which comprises $SnO_2 \cdot xH_2O$ wherein $x \geq 0$ dispersed in tetraalkyl ammonium hydroxide wherein the tetraalkyl ammonium hydroxide is defined by the following formula:

$$(C_nH_{2n+1})_4NOH$$

wherein $5 \geq n \geq 1$.

* * * * *

UNITED STATES PATENT AND TRADEMARK OFFICE
CERTIFICATE OF CORRECTION

PATENT NO.   : 6,087,524  
DATED        : July 11, 2000  
INVENTOR(S)  : James Frank Brazdil, Jr., Joseph Peter Bartek Page 1 of 1

It is certified that error appears in the above-identified patent and that said Letters Patent is hereby corrected as shown below:

At the top of the Title Page and in Column 1, Line 3, "$SNO_2 \cdot XH_2O$" should read: "$SnO_2 \cdot xH_2O$"

Column 2, Line 52, "is one or more" should read: "D is one or more"

Signed and Sealed this

Twelfth Day of June, 2001

*Attest:*

*Attesting Officer*

NICHOLAS P. GODICI  
*Acting Director of the United States Patent and Trademark Office*